United States Patent
Ni et al.

(10) Patent No.: US 10,315,973 B2
(45) Date of Patent: Jun. 11, 2019

(54) METHOD FOR PREPARING ETHYLENE GLYCOL BY HYDROLYSING ETHYLENE GLYCOL MONOMETHYL ETHER

(71) Applicant: Dalian Institute of Chemical Physics, Chinese Academy of Sciences, Dalian (CN)

(72) Inventors: Youming Ni, Dalian (CN); Wenliang Zhu, Dalian (CN); Yong Liu, Dalian (CN); Hongchao Liu, Dalian (CN); Lei Shi, Dalian (CN); Zhongmin Liu, Dalian (CN)

(73) Assignee: Dalian Institute of Chemical Physics, Chinese Academy of Sciences, Dalian (CN)

( * ) Notice: Subject to any disclaimer, the term of this patent is extended or adjusted under 35 U.S.C. 154(b) by 0 days.

(21) Appl. No.: 15/763,296

(22) PCT Filed: Dec. 8, 2015

(86) PCT No.: PCT/CN2015/096645
§ 371 (c)(1),
(2) Date: Mar. 26, 2018

(87) PCT Pub. No.: WO2017/054317
PCT Pub. Date: Apr. 6, 2017

(65) Prior Publication Data
US 2018/0201557 A1  Jul. 19, 2018

(30) Foreign Application Priority Data
Sep. 30, 2015  (CN) .......................... 2015 1 0644148

(51) Int. Cl.
*C07C 29/10* (2006.01)
*C07C 31/20* (2006.01)
(Continued)

(52) U.S. Cl.
CPC ............. *C07C 29/10* (2013.01); *B01J 29/088* (2013.01); *B01J 29/185* (2013.01); *B01J 29/405* (2013.01);
(Continued)

(58) Field of Classification Search
CPC ........ C07C 29/10; C07C 31/202; B01J 39/05; B01J 29/088; B01J 29/185; B01J 29/405;
(Continued)

(56) References Cited

U.S. PATENT DOCUMENTS

| 4,806,658 A | * | 2/1989 | Chang | ..................... C07C 29/10 549/368 |
| 7,754,926 B2 | * | 7/2010 | Kibino | ..................... C07C 29/10 568/678 |
| 2010/0105947 A1 | | 4/2010 | Celik et al. | |

FOREIGN PATENT DOCUMENTS

| CN | 103172516 A | 6/2013 |
| CN | 103172517 A | 6/2013 |

(Continued)

OTHER PUBLICATIONS

Payra, P., et al., Zeolites: a Primer, 2003, Marcel Dekker, Inc., Handbood of Zeolite Science and Technology, Chapter 1, 19 pages (Year: 2003).*

(Continued)

*Primary Examiner* — Yate' K Cutliff
(74) *Attorney, Agent, or Firm* — Edwin A. Sisson, Attorney at Law, LLC; Jeffrey J. Banyas

(57) ABSTRACT

This invention provides a method for preparing ethylene glycol by hydrolyzing ethylene glycol monomethyl ether. The method comprises passing a fresh raw material containing ethylene glycol monomethyl ether and water through a reaction zone loaded with a solid acid catalyst to react under the following conditions; separating the reacted mix- (Continued)

ture via a separation system to obtain a target product of ethylene glycol, by-products containing methanol, dimethyl ether and ethylene glycol-based derivatives, and an unreacted raw material containing ethylene glycol monomethyl ether and water; passing the target product of ethylene glycol into a product collection system; and passing methyl alcohol and dimethyl ether in the by-products into a by-product collection system; and after being mixed with the fresh raw materials containing ethylene glycol monomethyl ether and water, the ethylene glycol-based derivatives in the by-products and the unreacted raw material containing ethylene glycol monomethyl ether and water being recycled into the reaction zone, to realize the preparation of ethylene glycol by hydrolyzing ethylene glycol monomethyl ether. This invention provides a new process to realize the preparation of ethylene glycol by hydrolyzing ethylene glycol monomethyl ether. And in the method, the catalyst has long life and good stability.

14 Claims, 1 Drawing Sheet

(51) Int. Cl.
*B01J 29/70* (2006.01)
*B01J 39/05* (2017.01)
*B01J 29/08* (2006.01)
*B01J 29/18* (2006.01)
*B01J 29/40* (2006.01)
*B01J 29/65* (2006.01)
*B01J 31/02* (2006.01)

(52) U.S. Cl.
CPC ............. *B01J 29/655* (2013.01); *B01J 29/70* (2013.01); *B01J 29/7057* (2013.01); *B01J 29/7088* (2013.01); *B01J 31/0227* (2013.01); *B01J 39/05* (2017.01); *C07C 31/202* (2013.01); *C07C 2529/08* (2013.01); *C07C 2529/18* (2013.01); *C07C 2529/40* (2013.01); *C07C 2529/65* (2013.01); *C07C 2529/70* (2013.01); *C07C 2531/025* (2013.01); *Y02P 20/52* (2015.11)

(58) Field of Classification Search
CPC ...... B01J 29/655; B01J 29/70; B01J 29/7057; B01J 29/7088; B01J 29/0227
See application file for complete search history.

(56) References Cited

FOREIGN PATENT DOCUMENTS

| | | | |
|---|---|---|---|
| CN | 103894228 A | 7/2014 | |
| CN | 104119228 A | 10/2014 | |
| CN | 104725224 A | 6/2015 | |
| EP | 0088529 A2 | 9/1983 | |
| GB | 2070002 A * | 9/1981 | ............ C07C 29/10 |
| WO | 2010/048300 A1 | 4/2010 | |

OTHER PUBLICATIONS

Celik et al., "Vapor-Phase Carbonylation of Dimethoxymethane over H-Faujasite", Angewandte Chemie, 2009, pp. 4813 to 4815, vol. 48, Wiley-VCH Verlag GmbH & Co. KGaA.
Celik et al., "Effect of zeolite framework type and Si/Al ratio on dimethoxymethane carbonylation", Journal of Catalysis, Jan. 29, 2010, pp. 185 to 195, vol. 270, Elsevier.
Celik et al., "An investigation into the mechanism and kinetics of dimethoxymethane carbonylation over FAU and MFI zeolites", Journal of Catalysis, Aug. 2, 2010, pp. 150 to 162, vol. 274, Elsevier.

* cited by examiner

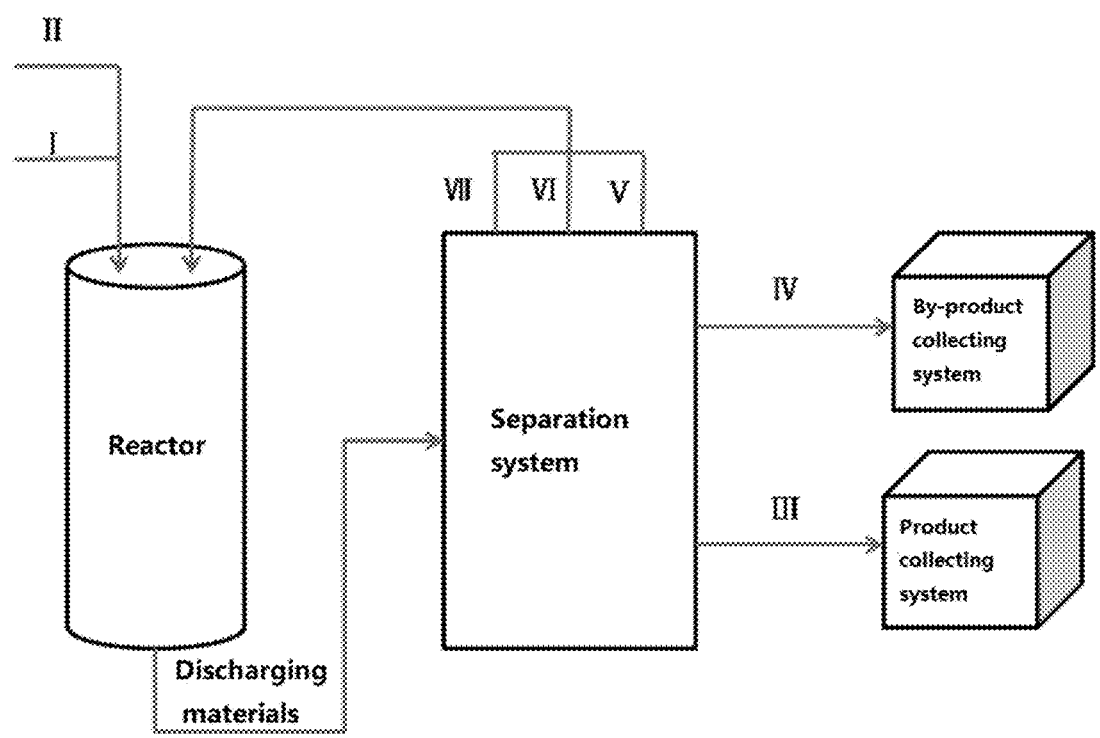

METHOD FOR PREPARING ETHYLENE GLYCOL BY HYDROLYSING ETHYLENE GLYCOL MONOMETHYL ETHER

PRIORITIES AND CROSS REFERENCES

This Application claims priority from International Application No. PCT/CN2015/096645 filed on 8 Dec. 2015 and Chinese Application No. 201510644148.3 filed on 30 Sep. 2015, the teachings of each of which are incorporated herein by reference in their entirety.

TECHNICAL FIELD

This invention refers to a method for preparing ethylene glycol by hydrolysing ethylene glycol monomethyl ether.

BACKGROUND

Ethylene glycol is an important chemical raw material and strategic material in China, which is used to produce polyester (which can be further processed to produce terelyene, PET bottles and thin films), explosives, glyoxal, and can also be used as antifreeze, plasticizers, hydraulic fluids, solvents and the like. In 2009, the import quantum of ethylene glycol in China was over 5.80 million tons. It is predicted that in 2015, ethylene glycol demand of China will reach 11.20 million tons; while the production capacity will be about 5 million tons, and the supply and demand gap will still be 6.20 million tons. Therefore, there is a good market prospect for the development and application of new production technology of ethylene glycol in China. Internationally, ethylene glycol is mainly obtained by hydration of ethylene oxide which is mainly produced by oxidation of ethylene generated from petroleum cracking. In view of the current state of China's energy source structure of being rich in coal, lack in oil and gas, and the crude oil price being kept at a high level for a long time, the process for producing ethylene glycol from coal as a new technique in coal chemistry industry is the most practical choice of the coal chemistry industry in the future, because it can ensure the national energy safety and make full use of the coal resource in China.

At present, the relatively mature technology in China is a complete set of technology containing CO gas phase catalytic synthesis oxalate ester and catalytic hydrogenation synthesis of ethylene glycol from oxalate ester, developed by Fujian Institute of Research on the Structure of Matter, Chinese Academy of Sciences. In early December 2009, the coal-to-ethylene glycol project of GEM Chemical Company, Tongliao, Neimenggu with a yearly output of 200 thousand tons, has been successful in getting through the entire process in the first-stage project and produced a qualified ethylene glycol product, which is the world first industrial demonstration device, attracting industry attention. However, due to relatively more industrial units, high requirement of industrial gases purity, usage of noble metal catalysts in the process of oxidative coupling, and utilization of nitrogen compounds with potential environment pollution, the technology process has been restricted in economic efficiency, environmental protection, energy-saving performance and further industrial scale-up.

Recently, methyl methoxyacetate, as an important organic intermediate, has attracted wide attention. It can be prepared by gas phase carbonylation of methylal (*Angew. Chem. Int. Ed.*, 2009, 48, 4813-4815). Methyl methoxyacetate can be hydrogenated to prepare ethylene glycol monomethyl ether and ethylene glycol monomethyl ether can be hydrolysed to prepare ethylene glycol. In CN104119228A, the above content has just been mentioned in Background and there are no any informations on the detailed steps and process for preparing ethylene glycol by hydrolization of ethylene glycol monomethyl ether.

SUMMARY OF THE INVENTION

The purpose of the present invention is providing a new method for preparing ethylene glycol by hydrolysing ethylene glycol monomethyl ether.

Therefore, the present invention provides a method for preparing ethylene glycol by hydrolysing ethylene glycol monomethyl ether, which comprises:

passing a fresh raw material containing ethylene glycol monomethyl ether and water through a reaction zone loaded with a solid acid catalyst to react under the following conditions; separating the reacted mixture via a separation system to obtain a target product of ethylene glycol, by-products containing methanol, dimethyl ether and ethylene glycol-based derivatives, and an unreacted raw material containing ethylene glycol monomethyl ether and water;

passing the target product of ethylene glycol into a product collection system; and passing methyl alcohol and dimethyl ether in the by-products into a by-product collection system; and after being mixed with the fresh raw materials containing ethylene glycol monomethyl ether and water, the ethylene glycol-based derivatives in the by-products and the unreacted raw material containing ethylene glycol monomethyl ether and water being recycled into the reaction zone, to realize the preparation of ethylene glycol by hydrolysing ethylene glycol monomethyl ether;

wherein, the solid acid catalyst is one or two catalysts selected from the group consisting of acidic molecular sieve catalysts and acidic resin catalysts;

the reaction zone is constituted by one or more reactors which are connected in series and/or in parallel;

the ethylene glycol-based derivatives is one or more derivatives selected from the group consisting of ethylene glycol dimethyl ether, 1,4-dioxane, diethylene glycol monomethyl ether, diethylene glycol dimethyl ether, triethylene glycol monomethyl ether, triethylene glycol dimethyl ether, diethylene glycol and triethylene glycol;

the reaction conditions are listed as follows: the reaction temperature is in a range from 100° C. to 250° C., and the reaction pressure are in a range from 0.5 MPa to 10 MPa, and the weight hourly space velocity of ethylene glycol monomethyl ether in the fresh raw material is in a range from 0.1 $h^{-1}$ to 10 $h^{-1}$.

The acidic molecular sieve has a pore structure of 8 to 12 membered ring, and a pore channel system of 1 to 3 dimensions; preferably, the structure type of the acidic molecular sieve is one or more types selected from the group consisting of MWW, FER, MFI, MOR, FAU and BEA.

The acidic molecular sieve is one or more molecular sieves selected from the group consisting of MCM-22 molecular sieve, ZSM-35 molecular sieve, ZSM-5 molecular sieve, mordenite molecular sieve, Y molecular sieve and β molecular sieve.

The atom ratio of Si to Al in the acidic molecular sieve Si/Al is in a range from 2 to 80; preferably, Si/Al is in a range of 5 to 50.

The acidic molecular sieve comprises a metal and the mass fraction of the metal is in a range from 0.1% to 15%, preferably 0.1% to 4%.

The metal is one or more metals selected from the group consisting of alkali metal, alkaline earth metal and rare earth metal.

The acidic molecular sieve catalyst comprises a forming agent, and the mass fraction of the forming agent is in a range from 1% to 40%; preferably, the forming agent is one or more materials selected from the group consisting of aluminum oxide, silicon oxide and kaolin.

The acidic resin catalyst is one or more resins selected from the group consisting of perfluorinated sulfonic acid resin Nafion and strong acidic cation exchange resin.

The reaction conditions are listed as follows: the reaction temperature is in a range from 140° C. to 200° C., the reaction pressure are in a range from 2 MPa to 7 MPa, and the weight hourly space velocity of ethylene glycol monomethyl ether in the fresh raw material is in a range from 0.5 $h^{-1}$ to 4 $h^{-1}$.

The reactor is one or more reactors selected from the group consisting of tank reactor, fixed bed reactor, moving bed reactor and fluidized bed reactor.

The present invention provides a brand new method for preparing ethylene glycol, which can be used as an important segment in the industrial route for producing ethylene glycol by carbonylation, hydrogenation and hydrolysis of methyl methoxyacetate. Moreover, in the method, the catalyst has long life and good stability.

DESCRIPTION OF THE FIGURES

FIG. 1 is a brief process flow chart of an Example in the present invention; wherein I is ethylene glycol monomethyl ether in the fresh raw material; and II is water in the fresh raw material; and III is the target product of ethylene glycol, IV is methanol and dimethyl ether in the by-products; and V and VI are respectively ethylene glycol monomethyl ether and water in the unreacted material; and VII is ethylene glycol-based derivatives in the by-products.

DETAILED DESCRIPTION OF THE EMBODIMENT

In the method provided by the present invention, a fresh raw material containing ethylene glycol monomethyl ether and water is passed through a reaction zone (or a reactor) loaded with a solid acid catalyst, reacting under certain conditions; and the discharging material is separated via a separation system to obtain the target product of ethylene glycol, by-products containing methanol, dimethyl ether and ethylene glycol-based derivatives, and unreacted raw material of ethylene glycol monomethyl ether and unreacted raw material of water; and the target product of ethylene glycol is then passed into a product collection system, and the by-products containing methyl alcohol and dimethyl ether are then passed into a by-product collection system; and the unreacted raw material of ethylene glycol monomethyl ether, the unreacted raw material of water and the ethylene glycol-based derivatives in the by-products are then recycled into the reaction zone for reaction, after being mixed with the fresh raw materials containing ethylene glycol monomethyl ether and water, to realize the preparation of ethylene glycol by hydrolysing ethylene glycol monomethyl ether.

In the present invention, the following reaction is the major reaction occurring in the reaction zone: $CH_3OCH_2CH_2OH+H_2O \rightleftharpoons HOCH_2CH_2OH+CH_3OH$; wherein the target product is ethylene glycol and the by-product is methanol. Additionally, other side reactions may occur and generate ethylene glycol-based derivatives comprising any one or more derivatives selected from the group consisting of ethylene glycol dimethyl ether, 1,4-dioxane, diethylene glycol monomethyl ether, diethylene glycol dimethyl ether, triethylene glycol monomethyl ether, triethylene glycol dimethyl ether, diethylene glycol and triethylene glycol.

According to the present invention, because the unreacted raw materials may be recycled, there is no special limits for the molar ratio of ethylene glycol monomethyl ether to water in the fresh raw material entering the reaction zone. However, according to the above reaction, during the reaction system is in a steady state operation, the molar ratio of ethylene glycol monomethyl ether to water in the fresh raw material is best to be 1:1. It should be noted that, term "fresh raw material" is mentioned in a comparison to the unreacted ethylene glycol monomethyl ether and water from recycling, the term can be used interchangeably with terms "new feed raw materials" or "external feed raw materials".

In the present invention, the reaction zone comprises at least one reactor, or the reaction zone is constituted by multiple reactors which are connected in series and/or in parallel. Or the reaction region is constituted by one or more reactors which are connected in series and/or in parallel, namely that the reaction zone can be one or more reactors. Preferably, in the present invention, the reactor is selected from a tank reactor, a fixed bed reactor, a moving bed reactor or a fluidized bed reactor, which can realize continuous reaction. For example, a brief process flow chart is shown in FIG. 1, and the reaction zone is constituted of one stainless steel fixed bed reactor.

The separation system that can be used in the method of the present invention is a system known in the art, such as a rectifying towers, which can use 2-4 rectifying towers to separate the target product of ethylene glycol, by-products of methanol, dimethyl ether and ethylene glycol-based derivatives, and the unreacted raw material containing ethylene glycol monomethyl ether and water. Then a delivering pump is used to pass the target product of ethylene glycol to the product collecting system, and the by-products containing methanol and dimethyl ether are passed into the by-product collecting system. Then a high pressure delivering pump was used to recycle the unreacted raw material of ethylene glycol monomethyl ether, unreacted raw material of water and by-product of ethylene glycol-based derivatives into the reaction zone for reaction, after being mixed with the fresh raw materials containing ethylene glycol monomethyl ether and water.

The product collecting system and the by-product collecting system that can be used in the method of the present invention are those ones known in the art, such as storage silo and storage chest which are commonly used in the art. In the actual production process, by-products methanol and dimethyl ether are usually directly delivered to the upstream reactor, such as methylal preparation reactor, to serve as a raw material.

Preferably, in the present invention, the reaction conditions are listed as follows: the reaction temperature is in a range from 100° C. to 250° C., the reaction pressure are in a range from 0.5 MPa to 10 MPa, and the weight hourly space velocity of ethylene glycol monomethyl ether in the fresh raw material is in a range from 0.1 $h^{-1}$ to 10 $h^{-1}$. More preferably, the reaction conditions are listed as follows: the reaction temperature is in a range from 140° C. to 200° C., the reaction pressure are in a range from 2 MPa to 7 MPa, and the weight hourly space velocity of ethylene glycol monomethyl ether in the fresh raw material is in a range from 0.5 $h^{-1}$ to 4.0 $h^{-1}$.

Preferably, in the present invention, the solid acid catalyst is one or two catalysts selected from the group consisting of acidic molecular sieve catalysts and acidic resin catalysts; more preferably, the acidic molecular sieve has a pore structure of 8 to 12 membered ring, and a pore channel system of 1 to 3 dimensions; further more preferably, the pore structure of 8 to 12 membered ring means that pore window of the molecular sieve is a ring constituted of 8 to 12 T atoms, which interconnect with each other by T-O-T, wherein the T atoms are Si or Al atoms.

Preferably, in the present invention, the structure type of the acidic molecular sieve is one or more types selected from the group consisting of MWW, FER, MFI, MOR, FAU and BEA.

Preferably, in the present invention, the acidic molecular sieve is one or more molecular sieves selected from the group consisting of MCM-22 molecular sieve, ZSM-35 molecular sieve, ZSM-5 molecular sieve, mordenite molecular sieve, Y molecular sieve and β molecular sieve.

Preferably, in the present invention, the atom ratio of Si to Al in the acidic molecular sieve Si/Al is in a range from 2 to 80; more preferably, the atom ratio of Si to Al in the acidic molecular sieve Si/Al is in a range from 5 to 50.

Preferably, in the present invention, the acidic molecular sieve comprises a metal and the mass fraction of the metal is in a range from 0.1% to 15%; preferably the mass fraction of the metal is in a range from 0.1% to 4%.

Preferably, in the present invention, the metal is one or more metals selected from the group consisting of alkali metal, alkaline earth metal and rare earth metal; wherein the alkali metal includes lithium (Li), sodium (Na), potassium (K), rubidium (Rb), cesium (Cs) and the like; the alkaline earth metal includes beryllium (Be), magnesium (Mg), calcium (Ca), strontium (Sr), barium (Ba) and the like; the rare earth metal includes scandium (Sc), yttrium (Y), lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutecium (Lu) and the like.

Preferably, in the present invention, the metal is introduced into the acidic molecular sieve by one or more methods selected from the group consisting of in situ synthesis, impregnation and ion exchange. In the present invention, the metal existing as ions at the ion exchange sites, or existing as metallic oxides in the channel or on the surface of the molecular sieve.

Preferably, in the present invention, the acidic molecular sieve refers to H type molecular sieve or metal modified H type molecular sieve.

Preferably, in the present invention, the acidic molecular sieve experience or do not experience a post-treatment of desilication or dealumination. Wherein the desilication post-treatment is an alkaline solution treatment. The alkaline solutions usually used include aqueous solutions of sodium hydroxide, potassium hydroxide, ammonium hydroxide, sodium carbonate and sodium bicarbonate. The dealuminization post-treatment is an acid solution treatment or a steam treatment. The acid solutions usually used include aqueous solutions of hydrochloric acid, nitric acid, oxalic acid, citric acid and acetic acid. The steam treatment is usually operated at a treating temperature in a range from 400° C. to 700° C.

Preferably, in the present invention, the acidic molecular sieve may contain one or more structures selected from the group consisting of micrometer structure, nanometer structure, microporous structure and meso-microporous structure.

Preferably, in the present invention, the mass fraction of the forming agent contained in the acidic molecular sieve catalyst is in a range from 1% to 40%. More preferably, the forming agent contained in the acidic molecular sieve catalyst is one or more materials selected from the group consisting of aluminum oxide, silicon oxide and kaolin.

Preferably, in the present invention, the acidic resin catalyst is one or more resins selected from the group consisting of perfluorinated sulfonic acid resin Nafion and strong acidic cation exchange resin; wherein the strong acidic cation exchange resin is prepared by sulfonation with sulfuric acid and modification with any materials selected from F, Cl and Br of a copolymer of styrene divinylbenzene.

EXAMPLES

The present invention is further illustrated in combination with specific Examples as follows. It should be understood that, these Examples are only used for illustrate the present invention but not to limited the scope thereof.

Unless otherwise specified, raw material and catalyst employed in the Examples of the present invention are commercial purchased and directly used.

Preparation of the Catalyst

Na-type molecular sieve and resin employed in the following Examples are commercial purchased and directly used.

Example 1

Na-type MCM-22 molecular sieve (Si/Al=5) was exchanged with 0.8 mol/L of ammonium nitrate aqueous solution at 80° C. for three times to obtain an ammonium-type mordenite. Then the ammonium-type mordenite was calcined at 500° C. for 4 h to obtain an H-type MCM-22 molecular sieve. The H-type MCM-22 molecular sieve was then pressed, crushed and sieved to 5-10 mesh and used as catalyst A.

Example 2

Na-type ZSM-35 molecular sieve (Si/Al=30) was exchanged with 0.8 mol/L of ammonium nitrate aqueous solution at 80° C. for three times to obtain an ammonium-type ZSM-35 molecular sieve. Then the ammonium-type ZSM-35 molecular sieve was calcined at 500° C. for 4 h to obtain an H-type ZSM-35 molecular sieve. The H-type ZSM-5 molecular sieve was then pressed, crushed and sieved to 5-10 mesh and used as catalyst B.

Example 3

Na-type ZSM-5 molecular sieve (Si/Al=50) was exchanged with 0.8 mol/L of ammonium nitrate aqueous solution at 80° C. for three times to obtain an ZSM-5 molecular sieve. Then the ammonium-type ZSM-35 molecular sieve was calcined at 500° C. for 4 h to obtain an H-type ZSM-35 molecular sieve. The H-type ZSM-5 molecular sieve was then pressed, crushed and sieved to 5-10 mesh and used as catalyst C.

Example 4

Na-type mordenite molecular sieve (Si/Al=15) was exchanged with 0.8 mol/L of ammonium nitrate aqueous solution at 80° C. for three times to obtain an ammonium-type mordenite molecular sieve. Then the ammonium-type mordenite molecular sieve was calcined at 500° C. for 4 h to obtain an H-type mordenite molecular sieve. The H-type mordenite molecular sieve was then pressed, crushed and sieved to 5-10 mesh and used as catalyst D.

Example 5

Na-type Y molecular sieve (Si/Al=2) was exchanged with 0.8 mol/L of ammonium nitrate aqueous solution at 80° C. for three times to obtain an ammonium-type Y molecular sieve. Then the ammonium-type Y molecular sieve was calcined at 500° C. for 4 h to obtain an H-type Y molecular sieve. The H-type Y molecular sieve was then pressed, crushed and sieved to 5-10 mesh and used as catalyst E.

Example 6

Na-type β molecular sieve (Si/Al=80) was exchanged with 0.8 mol/L of ammonium nitrate aqueous solution at 80° C. for three times to obtain an ammonium-type β molecular sieve. Then the ammonium-type β molecular sieve was calcined at 500° C. for 4 h to obtain an H-type β molecular sieve. The H-type β molecular sieve was then pressed, crushed and sieved to 5-10 mesh and used as catalyst F.

Example 7

Na-type ZSM-5 molecular sieve (Si/Al=50) was exchanged with 0.8 mol/L of ammonium nitrate aqueous solution at 80° C. for three times to obtain an ZSM-5 molecular sieve. The ammonium-type ZSM-5 molecular sieve was equivalent-volume impregnated with lanthanum nitrate aqueous solution, then kept at room temperature for 24 h. And after being dried and calcined at 500° C. in air atmosphere for 4 h, a sample of H-type ZSM-5 molecular sieve containing 1% lanthanum (mass fraction) was obtained. Then the sample was extruded with 20% aluminum oxide to form a rod like acidic ZSM-5 molecular sieve containing lanthanum of Φ 3 mm×3 mm, which was used as catalyst G.

Example 8

Na-type β molecular sieve (Si/Al=80) was exchanged with 0.8 mol/L of ammonium nitrate aqueous solution at 80° C. for three times to obtain an ammonium-type β molecular sieve. The ammonium-type β molecular sieve was equivalent-volume impregnated with calcium nitrate aqueous solution, then kept at room temperature for 24 h. And after being dried and calcined at 500° C. in air atmosphere for 4 h, a sample of H-type β molecular sieve containing 1% calcium (mass fraction) was obtained. Then the sample was extruded with 20% aluminum oxide to form a rod like acidic β molecular sieve containing calcium of Φ 3 mm×3 mm, which was used as catalyst H.

Example 9

Na-type Y molecular sieve (Si/Al=2) was exchanged with 0.8 mol/L of ammonium nitrate aqueous solution at 80° C. for three times to obtain an ammonium-type Y molecular sieve. The ammonium-type β molecular sieve was equivalent-volume impregnated with cesium nitrate aqueous solution, then kept at room temperature for 24 h. And after being dried and calcined at 500° C. in air atmosphere for 4 h, a sample of H-type Y molecular sieve containing 0.5% cesium (mass fraction) was obtained. Then the sample was extruded with 20% aluminum oxide to form a rod like acidic Y molecular sieve containing cesium of Φ 3 mm×3 mm, which was used as catalyst I.

Example 10

Macroporous strong acidic cation exchange resin D005 (produced by Mingzhu special resin Co. Ltd Dandong) was immersed in 0.1 mol/L sulfuric acid aqueous solution for 4 h at room temperature, and after being filtered and dried at 100° C., an acidic resin was obtained, which was used as catalyst J.

Example 11

Perfluorinated sulfonic acid resin Nafion (produced by E.I. Du Pont Company) was immersed in 0.1 mol/L sulfuric acid aqueous solution for 4 h at room temperature, and after being filtered and dried at 100° C., an acidic resin was obtained, which was used as catalyst K.

Preparation of Ethylene Glycol and Test of the Catalyst Performance

Example 12

In accordance with the process flow shown in FIG. 1, 10 kg of catalyst A was loaded into a stainless steel fixed bed reactor with inner diameter of 20 cm and a height of 60 cm. In order to reduce dead volume and make the fluid homogeneously distribute, the non-catalytic volume in the reactor was filled with quartz sands. In the reactor, the reaction temperature in the reactor was 140° C., and the reaction pressure was 2 MPa, and when the reaction system was in a steady state operation, the feed flow rate of ethylene glycol monomethyl ether in the fresh raw material was 20 kg/h and the weight hourly space velocity of ethylene glycol monomethyl ether in the fresh raw material was 2.0 h$^{-1}$. And the feed flow rate of water in the fresh raw material was 4.7 kg/h. The discharging material of the reaction was separated by a separation system mainly constituted of four rectifying towers. The flow rate of ethylene glycol monomethyl ether in the recycled raw material was 10 kg/h, and the flow rate of water in the recycled raw material was 7.1 kg/h, and the flow rate of ethylene glycol dimethyl ether in the recycled by-products was 1.2 kg/h, and the flow rate of diethylene glycol monomethyl ether in the recycled by-products was 0.2 kg/h, and the flow rate of diethylene glycol dimethyl ether in the recycled by-products was 0.1 kg/h, and the flow rate of diethylene glycol in the recycled by-products was 0.03 kg/h, and the flow rate of 1,4-dioxane in the recycled by-products was 0.01 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 16.3 kg/h, and the flow rate of the by-product methanol was 8.2 kg/h, and the flow rate of the by-product dimethyl ether was 0.1 kg/h. The catalytic performance of the catalyst essentially stay unchanged after running for 2000 h in a steady state operation.

Example 13

In accordance with the process flow shown in FIG. 1, 10 kg of catalyst B was loaded into a stainless steel fixed bed reactor with inner diameter of 20 cm and a height of 60 cm. In order to reduce dead volume and make the fluid homogeneously distribute, the non-catalytic volume in the reactor was filled with quartz sands. In the reactor, the reaction temperature in the reactor was 200° C., and the reaction pressure was 7 MPa, and when the reaction system was in a steady state operation, the feed flow rate of ethylene glycol monomethyl ether in the fresh raw material was 40 kg/h and the weight hourly space velocity of ethylene glycol monomethyl ether in the fresh raw material was 4.0 $h^{-1}$. And the feed flow rate of water in the fresh raw material was 9.5 kg/h. The discharging material of the reaction was separated by a separation system mainly constituted of four rectifying towers. The flow rate of ethylene glycol monomethyl ether in the recycled raw material was 15 kg/h, and the flow rate of water in the recycled raw material was 10 kg/h, and the flow rate of ethylene glycol dimethyl ether in the recycled by-products was 1.0 kg/h, and the flow rate of diethylene glycol monomethyl ether in the recycled by-products was 0.1 kg/h, and the flow rate of diethylene glycol dimethyl ether in the recycled by-products was 0.1 kg/h, and the flow rate of diethylene glycol in the recycled by-products was 0.02 kg/h, and the flow rate of 1,4-dioxane in the recycled by-products was 0.02 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 32.6 kg/h, and the flow rate of the by-product methanol was 16.6 kg/h, and the flow rate of the by-product dimethyl ether was 0.1 kg/h. The catalytic performance of the catalyst essentially stay unchanged after running for 2000 h in a steady state operation.

Example 14

In accordance with the process flow shown in FIG. 1, 10 kg of catalyst C was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 250° C., and the reaction pressure was 0.5 MPa, and when the reaction system was in a steady state operation, the feed flow rate of ethylene glycol monomethyl ether in the fresh raw material was 1 kg/h and the weight hourly space velocity of ethylene glycol monomethyl ether in the fresh raw material was 0.1 $h^{-1}$. And the feed flow rate of water in the fresh raw material was 0.24 kg/h. The discharging material of the reaction was separated by a separation system mainly constituted of four rectifying towers. The flow rate of ethylene glycol monomethyl ether in the recycled raw material was 4 kg/h, and the flow rate of water in the recycled raw material was 3 kg/h, and the flow rate of ethylene glycol dimethyl ether in the recycled by-products was 0.2 kg/h, and the flow rate of diethylene glycol monomethyl ether in the recycled by-products was 0.2 kg/h, and the flow rate of diethylene glycol dimethyl ether in the recycled by-products was 0.1 kg/h, and the flow rate of diethylene glycol in the recycled by-products was 0.01 kg/h, and the flow rate of 1,4-dioxane in the recycled by-products was 0.02 kg/h, and the flow rate of triethylene glycol monomethyl ether in the recycled by-products was 0.02 kg/h, and the flow rate of triethylene glycol dimethyl ether in the recycled by-products was 0.01 kg/h. The flow rate of the product ethylene glycol was 0.82 kg/h, and the flow rate of the by-product methanol was 0.40 kg/h, and the flow rate of the by-product dimethyl ether was 0.1 kg/h. The catalytic performance of the catalyst essentially stay unchanged after running for 2000 h in a steady state operation.

Example 15

In accordance with the process flow shown in FIG. 1, 10 kg of catalyst D was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 100° C., and the reaction pressure was 10 MPa, and when the reaction system was in a steady state operation, the feed flow rate of ethylene glycol monomethyl ether in the fresh raw material was 5 kg/h and the weight hourly space velocity of ethylene glycol monomethyl ether in the fresh raw material was 0.5 $h^{-1}$. And the feed flow rate of water in the fresh raw material was 1.18 kg/h. The discharging material of the reaction was separated by a separation system mainly constituted of four rectifying towers. The flow rate of ethylene glycol monomethyl ether in the recycled raw material was 5 kg/h, and the flow rate of water in the recycled raw material was 4 kg/h, and the flow rate of ethylene glycol dimethyl ether in the recycled by-products was 0.4 kg/h, and the flow rate of diethylene glycol monomethyl ether in the recycled by-products was 0.1 kg/h, and the flow rate of diethylene glycol dimethyl ether in the recycled by-products was 0.05 kg/h, and the flow rate of diethylene glycol in the recycled by-products was 0.02 kg/h, and the flow rate of 1,4-dioxane in the recycled by-products was 0.01 kg/h, and the flow rate of triethylene glycol monomethyl ether in the recycled by-products was 0.03 kg/h, and the flow rate of triethylene glycol dimethyl ether in the recycled by-products was 0.01 kg/h. The flow rate of the product ethylene glycol was 4.08 kg/h, and the flow rate of the by-product methanol was 2.0 kg/h, and the flow rate of the by-product dimethyl ether was 0.1 kg/h. The catalytic performance of the catalyst essentially stay unchanged after running for 2000 h in a steady state operation.

Example 16

In accordance with the process flow shown in FIG. 1, 10 kg of catalyst E was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 250° C., and the reaction pressure was 10 MPa, and when the reaction system was in a steady state operation, the feed flow rate of ethylene glycol monomethyl ether in the fresh raw material was 100 kg/h and the weight hourly space velocity of ethylene glycol monomethyl ether in the fresh raw material was 10 $h^{-1}$. And the feed flow rate of water in the fresh raw material was 23.7 kg/h. The discharging material of the reaction was separated by a separation system mainly constituted of four rectifying towers. The flow rate of ethylene glycol monomethyl ether in the recycled raw material was 50 kg/h, and the flow rate of water in the recycled raw material was 100 kg/h, and the flow rate of ethylene glycol dimethyl ether in the recycled by-products was 4.0 kg/h, and the flow rate of diethylene glycol monomethyl ether in the recycled by-products was 1.3 kg/h, and the flow rate of diethylene glycol dimethyl ether in the recycled by-products was 0.8 kg/h, and the flow rate of diethylene glycol in the recycled by-products was 0.3 kg/h, and the flow rate of 1,4-dioxane in the recycled by-products was 0.2 kg/h, and the flow rate of triethylene glycol monomethyl ether in the recycled by-products was 0.2 kg/h, and the flow rate of triethylene glycol dimethyl ether in the recycled by-products was 0.1 kg/h. Flow rate of the product ethylene glycol was 81.6 kg/h, flow rate of the by-product methanol was 42.0 kg/h, flow rate of the by-product dimethyl ether was 0.2 kg/h. The catalytic performance of the catalyst essentially stay unchanged after operated 2000 h under a steady state.

Example 17

In accordance with the process flow shown in FIG. 1, 10 kg of catalyst F was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 220° C., and the reaction pressure was 3 MPa, and when the reaction system was in a steady state operation, the feed flow rate of ethylene glycol monomethyl ether in the fresh raw material was 50 kg/h and the weight hourly space velocity of ethylene glycol monomethyl ether in the fresh raw material was 5 $h^{-1}$. And the feed flow rate of water in the fresh raw material was 11.8 kg/h. The discharging material of the reaction was separated by a separation system mainly constituted of four rectifying towers. The flow rate of ethylene glycol monomethyl ether in the recycled raw material was 20 kg/h, and the flow rate of water in the recycled raw material was 70 kg/h, and the flow rate of ethylene glycol dimethyl ether in the recycled by-products was 2.0 kg/h, and the flow rate of diethylene glycol monomethyl ether in the recycled by-products was 0.3 kg/h, and the flow rate of diethylene glycol dimethyl ether in the recycled by-products was 0.4 kg/h, and the flow rate of diethylene glycol in the recycled by-products was 0.2 kg/h, and the flow rate of 1,4-dioxane in the recycled by-products was 0.2 kg/h, and the flow rate of triethylene glycol monomethyl ether in the recycled by-products was 0.2 kg/h, and the flow rate of triethylene glycol dimethyl ether in the recycled by-products was 0.1 kg/h. The flow rate of the product ethylene glycol was 4.08 kg/h, and the flow rate of the by-product methanol was 20.9 kg/h, and the flow rate of the by-product dimethyl ether was 0.2 kg/h. The catalytic performance of the catalyst essentially stay unchanged after running for 2000 h in a steady state operation.

Example 18

In accordance with the process flow shown in FIG. 1, 10 kg of catalyst G was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 160° C., and the reaction pressure was 2 MPa, and when the reaction system was in a steady state operation, the feed flow rate of ethylene glycol monomethyl ether in the fresh raw material was 20 kg/h and the weight hourly space velocity of ethylene glycol monomethyl ether in the fresh raw material was 2.0 $h^{-1}$. And the feed flow rate of water in the fresh raw material was 4.7 kg/h. The discharging material of the reaction was separated by a separation system mainly constituted of four rectifying towers. The flow rate of ethylene glycol monomethyl ether in the recycled raw material was 9 kg/h, and the flow rate of water in the recycled raw material was 6 kg/h, and the flow rate of ethylene glycol dimethyl ether in the recycled by-products was 1.1 kg/h, and the flow rate of diethylene glycol monomethyl ether in the recycled by-products was 0.2 kg/h, and the flow rate of diethylene glycol dimethyl ether in the recycled by-products was 0.2 kg/h, and the flow rate of diethylene glycol in the recycled by-products was 0.03 kg/h, and the flow rate of 1,4-dioxane in the recycled by-products was 0.01 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 16.3 kg/h, and the flow rate of the by-product methanol was 8.2 kg/h, and the flow rate of the by-product dimethyl ether was 0.1 kg/h. The catalytic performance of the catalyst essentially stay unchanged after running for 2000 h in a steady state operation.

Example 19

In accordance with the process flow shown in FIG. 1, 10 kg of catalyst H was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 170° C., and the reaction pressure was 3 MPa, and when the reaction system was in a steady state operation, the feed flow rate of ethylene glycol monomethyl ether in the fresh raw material was 20 kg/h and the weight hourly space velocity of ethylene glycol monomethyl ether in the fresh raw material was 2.0 $h^{-1}$. And the feed flow rate of water in the fresh raw material was 4.7 kg/h. The discharging material of the reaction was separated by a separation system mainly constituted of four rectifying towers. The flow rate of ethylene glycol monomethyl ether in the recycled raw material was 8.8 kg/h, and the flow rate of water in the recycled raw material was 5.7 kg/h, and the flow rate of ethylene glycol dimethyl ether in the recycled by-products was 1.0 kg/h, and the flow rate of diethylene glycol monomethyl ether in the recycled by-products was 0.3 kg/h, and the flow rate of diethylene glycol dimethyl ether in the recycled by-products was 0.3 kg/h, and the flow rate of diethylene glycol in the recycled by-products was 0.04 kg/h, and the flow rate of 1,4-dioxane in the recycled by-products was 0.02 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 16.2 kg/h, and the flow rate of the by-product methanol was 8.1 kg/h, and the flow rate of the by-product dimethyl ether was 0.2 kg/h. The catalytic performance of the catalyst essentially stay unchanged after running for 2000 h in a steady state operation.

Example 20

In accordance with the process flow shown in FIG. 1, 10 kg of catalyst I was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 180° C., and the reaction pressure was 3 MPa, and when the reaction system was in a steady state operation, the feed flow rate of ethylene glycol monomethyl ether in the fresh raw material was 50 kg/h and the weight hourly space velocity of ethylene glycol monomethyl ether in the fresh raw material was 5 h$^{-1}$. And the feed flow rate of water in the fresh raw material was 11.8 kg/h. The discharging material of the reaction was separated by a separation system mainly constituted of four rectifying towers. The flow rate of ethylene glycol monomethyl ether in the recycled raw material was 18 kg/h, and the flow rate of water in the recycled raw material was 60 kg/h, and the flow rate of ethylene glycol dimethyl ether in the recycled by-products was 1.7 kg/h, and the flow rate of diethylene glycol monomethyl ether in the recycled by-products was 0.3 kg/h, and the flow rate of diethylene glycol dimethyl ether in the recycled by-products was 0.4 kg/h, and the flow rate of diethylene glycol in the recycled by-products was 0.2 kg/h, and the flow rate of 1,4-dioxane in the recycled by-products was 0.2 kg/h, and the flow rate of triethylene glycol monomethyl ether in the recycled by-products was 0.2 kg/h, and the flow rate of triethylene glycol dimethyl ether in the recycled by-products was 0.1 kg/h. The flow rate of the product ethylene glycol was 40.8 kg/h, and the flow rate of the by-product methanol was 20.9 kg/h, and the flow rate of the by-product dimethyl ether was 0.2 kg/h. The catalytic performance of the catalyst essentially stay unchanged after running for 2000 h in a steady state operation.

Example 21

In accordance with the process flow shown in FIG. 1, 10 kg of catalyst J was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 120° C., and the reaction pressure was 6 MPa, and when the reaction system was in a steady state operation, the feed flow rate of ethylene glycol monomethyl ether in the fresh raw material was 30 kg/h and the weight hourly space velocity of ethylene glycol monomethyl ether in the fresh raw material was 3.0 h$^{-1}$. And the feed flow rate of water in the fresh raw material was 7.1 kg/h. The discharging material of the reaction was separated by a separation system mainly constituted of four rectifying towers. The flow rate of ethylene glycol monomethyl ether in the recycled raw material was 11 kg/h, and the flow rate of water in the recycled raw material was 8 kg/h, and the flow rate of ethylene glycol dimethyl ether in the recycled by-products was 0.7 kg/h, and the flow rate of diethylene glycol monomethyl ether in the recycled by-products was 0.1 kg/h, and the flow rate of diethylene glycol dimethyl ether in the recycled by-products was 0.1 kg/h, and the flow rate of diethylene glycol in the recycled by-products was 0.02 kg/h, and the flow rate of 1,4-dioxane in the recycled by-products was 0.02 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 24.4 kg/h, and the flow rate of the by-product methanol was 12.5 kg/h, and the flow rate of the by-product dimethyl ether was 0.1 kg/h. The catalytic performance of the catalyst essentially stay unchanged after running for 2000 h in a steady state operation.

Example 22

In accordance with the process flow shown in FIG. 1, 10 kg of catalyst K was loaded into a stainless steel fixed bed reactor with inner diameter of 20 cm and a height of 60 cm. In order to reduce dead volume and to make the fluid homogeneously distribute, the non-catalytic volume in the reactor was filled with quartz sands. In the reactor, the reaction temperature in the reactor was 125° C., and the reaction pressure was 1 MPa, and when the reaction system was in a steady state operation, the feed flow rate of ethylene glycol monomethyl ether in the fresh raw material was 15 kg/h and the weight hourly space velocity of ethylene glycol monomethyl ether in the fresh raw material was 1.5 h$^{-1}$. And the feed flow rate of water in the fresh raw material was 3.6 kg/h. The discharging material of the reaction was separated by a separation system mainly constituted of four rectifying towers. The flow rate of ethylene glycol monomethyl ether in the recycled raw material was 2.0 kg/h, and the flow rate of water in the recycled raw material was 3.5 kg/h, and the flow rate of ethylene glycol dimethyl ether in the recycled by-products was 0.4 kg/h, and the flow rate of diethylene glycol monomethyl ether in the recycled by-products was 0.2 kg/h, and the flow rate of diethylene glycol dimethyl ether in the recycled by-products was 0.1 kg/h, and the flow rate of diethylene glycol in the recycled by-products was 0.04 kg/h, and the flow rate of 1,4-dioxane in the recycled by-products was 0.01 kg/h, and the flow rate of triethylene glycol monomethyl ether in the recycled by-products was 0.01 kg/h, and the flow rate of triethylene glycol dimethyl ether in the recycled by-products was 0.01 kg/h. The flow rate of the product ethylene glycol was 12.2 kg/h, and the flow rate of the by-product methanol was 6.2 kg/h, and the flow rate of the by-product dimethyl ether was 0.1 kg/h. The catalytic performance of the catalyst essentially stay unchanged after running for 2000 h in a steady state operation.

The present invention has been described in detail as above, but the invention is not limited to the detailed embodiments described in this text. Those skilled in the art will understand that other changes and deformations can be made without deviating from the scope of the invention. The scope of the invention is limited by the appended claims.

The invention claimed is:

1. A method for preparing ethylene glycol by hydrolysing ethylene glycol monomethyl ether, which comprises:
    passing a fresh raw material containing ethylene glycol monomethyl ether and water through a reaction zone loaded with a solid acid catalyst to react under the following conditions: the reaction temperature is in a range from 100° C. to 250° C., and the reaction pressure are in a range from 0.5 MPa to 10 MPa, and the weight hourly space velocity of ethylene glycol monomethyl ether in the fresh raw material is in a range from 0.1h$^{-1}$ to 10 h$^{-1}$; separating the reacted mixture via a separation system to obtain a target product of ethylene glycol, by-products containing methanol, dimethyl ether and ethylene glycol-based derivatives, and an unreacted raw material containing ethylene glycol monomethyl ether and water; and
    passing the target product of ethylene glycol into a product collection system; and passing methyl alcohol and dimethyl ether in the by-products into a by-product collection system; and after being mixed with the fresh raw materials containing ethylene glycol monomethyl ether and water, the ethylene glycol-based derivatives in the by-products and the unreacted raw material containing ethylene glycol monomethyl ether and water being recycled into the reaction zone, to realize the preparation of ethylene glycol by hydrolysing ethylene glycol monomethyl ether;

wherein, the solid acid catalyst is one or two catalysts selected from the group consisting of acidic molecular sieve catalysts and acidic resin catalysts; and the ethylene glycol-based derivatives is one or more derivatives selected from the group consisting of ethylene glycol dimethyl ether, 1,4-dioxane, diethylene glycol monomethyl ether, diethylene glycol dimethyl ether, triethylene glycol monomethyl ether, triethylene glycol dimethyl ether, diethylene glycol and triethylene glycol.

2. The method according to claim 1, wherein the acidic molecular sieve has a pore structure of 8 to 12 membered ring and a pore channel system of 1 to 3 dimensions.

3. The method according to claim 2, wherein the acidic molecular sieve is one or more molecular sieves selected from the group consisting of MCM-22 molecular sieve, ZSM-35 molecular sieve, ZSM-5 molecular sieve, mordenite molecular sieve, Y molecular sieve and β molecular sieve.

4. The method according to claim 1, wherein the atom ratio of Si to Al in the acidic molecular sieve Si/Al is in a range from 2 to 80.

5. The method according to claim 1, wherein the acidic molecular sieve comprises a metal and the mass fraction of the metal is in a range from 0.1% to 15%.

6. The method according to claim 5, wherein the metal is one or more metals selected from the group consisting of alkali metal, alkaline earth metal and rare earth metal.

7. The method according to claim 1, wherein the acidic molecular sieve catalyst comprises a forming agent, and the mass fraction of the forming agent is in a range from 1% to 40%.

8. The method according to claim 1, wherein the acidic resin catalyst is one or more resins selected from the group consisting of perfluorinated sulfonic acid resin Nafion and strong acidic cation exchange resin.

9. The method according to claim 1, wherein the conditions are listed as follows: the reaction temperature is in a range from 140° C. to 200° C., the reaction pressure are in a range from 2 MPa to 7 MPa, and the weight hourly space velocity of ethylene glycol monomethyl ether in the fresh raw material is in a range from $0.5h^{-1}$ to $4h^{-1}$.

10. The method according to claim 1, wherein the reactor is one or more reactors selected from the group consisting of tank reactor, fixed bed reactor, moving bed reactor and fluidized bed reactor.

11. The method according to claim 1, wherein the structure type of the acidic molecular sieve is one or more types selected from the group consisting of MWW, FER, MFI, MOR, FAU and BEA.

12. The method according to claim 1, wherein the atom ratio of Si to Al in the acidic molecular sieve Si/Al is in a range of 5 to 50.

13. The method according to claim 1, wherein the acidic molecular sieve comprises a metal and the mass fraction of the metal is in a range from 0.1% to 4%.

14. The method according to claim 7, wherein the forming agent is one or more materials selected from the group consisting of aluminum oxide, silicon oxide and kaolin.

* * * * *